(12) United States Patent
Mellul et al.

(10) Patent No.: US 8,097,571 B2
(45) Date of Patent: Jan. 17, 2012

(54) COMPOSITION CONTAINING AT LEAST ONE HYDROXY ACID, AT LEAST ONE MONO- OR DISACCHARIDE AND AT LEAST ONE CERAMIDE, AND METHODS

(75) Inventors: Myriam Mellul, L'Hay les Roses (FR); Jean-Michel Sturla, Boulogne (FR)

(73) Assignee: L'Oreal, Paris (FR)

( * ) Notice: Subject to any disclaimer, the term of this patent is extended or adjusted under 35 U.S.C. 154(b) by 564 days.

(21) Appl. No.: 11/686,968

(22) Filed: Mar. 16, 2007

(65) Prior Publication Data

US 2007/0226916 A1 Oct. 4, 2007

Related U.S. Application Data

(60) Provisional application No. 60/796,861, filed on May 3, 2006.

(30) Foreign Application Priority Data

Apr. 4, 2006 (FR) ...................................... 06 51187

(51) Int. Cl.
| | |
|---|---|
| *A61K 8/18* | (2006.01) |
| *A61K 8/00* | (2006.01) |
| *A61K 8/72* | (2006.01) |
| *A61K 8/30* | (2006.01) |
| *A61Q 1/14* | (2006.01) |
| *A61Q 19/00* | (2006.01) |
| *A61Q 19/10* | (2006.01) |
| *A61Q 5/10* | (2006.01) |
| *A61Q 5/00* | (2006.01) |
| *A61Q 9/00* | (2006.01) |
| *A61Q 7/00* | (2006.01) |
| *A61Q 5/12* | (2006.01) |
| *A61Q 5/04* | (2006.01) |
| *C11D 3/32* | (2006.01) |

(52) U.S. Cl. ...... 510/119; 510/130; 424/70.1; 424/70.2; 424/70.11; 424/70.12; 424/70.19; 424/70.21; 424/70.22; 424/70.27; 424/70.31; 8/405

(58) Field of Classification Search .................. 510/123, 510/119, 130; 424/443–449, 70.1–70.2, 424/70.11–70.12, 70.19, 70.21–70.22, 70.27, 424/70.31; 8/405

See application file for complete search history.

(56) References Cited

U.S. PATENT DOCUMENTS

| | | | |
|---|---|---|---|
| 6,350,441 B1 * | 2/2002 | Giles et al. ................. | 424/70.12 |
| 6,623,751 B2 * | 9/2003 | Gueret ......................... | 424/449 |
| 6,635,262 B2 * | 10/2003 | Jourdan et al. ............... | 424/400 |
| 7,157,413 B2 * | 1/2007 | Lazzeri et al. ............... | 510/119 |
| 2002/0182161 A1 * | 12/2002 | Ainger et al. ............... | 424/70.12 |
| 2003/0147842 A1 * | 8/2003 | Restle et al. ............. | 424/70.122 |
| 2003/0157049 A1 * | 8/2003 | Gawtrey et al. ........... | 424/70.122 |

FOREIGN PATENT DOCUMENTS

| | | | |
|---|---|---|---|
| DE | 12 20 969 | | 7/1966 |
| JP | 2004-250372 | | 9/2004 |
| JP | 2004 250372 | * | 9/2004 |
| WO | WO 2004/054525 | | 7/2004 |
| WO | WO 2004/054526 | | 7/2004 |
| WO | WO 2004/073663 | | 9/2004 |

OTHER PUBLICATIONS

Database WPI Week 2004, Derwent Publications Ltd., London, GB: AN 2004-184801, XP002407833, "First Agent for Wavy-Hair Correction, Contains Reduer, Alkali Chemicals, Gluconic Acid and Trehalose," JP 2004 026770 (Jan. 29, 2004).

Database WPI Week 2003, Derwent Publications Ltd., London, GB: AN 2003-527917, XP002407834, "Rinse for Hair Comprises Polysaccharide Containing Glucose, Fucose, Glucuronic Acid and/or Rhamnose as Main Comonents," JP 2003 089624 (Mar. 28, 2003).

* cited by examiner

*Primary Examiner* — Lorna M Douyon
*Assistant Examiner* — Tanisha Diggs
(74) *Attorney, Agent, or Firm* — Oblon, Spivak, McClelland, Maier & Neustadt, L.L.P.

(57) ABSTRACT

Composition which, in a preferred embodiment, contains, in a cosmetically acceptable medium, at least one monosaccharide and/or disaccharide, at least one α-hydroxy acid, and at least one ceramide compound. Uses include topical application for the treatment of keratinous substances, in particular keratinous fibres, especially the hair.

24 Claims, No Drawings

COMPOSITION CONTAINING AT LEAST ONE HYDROXY ACID, AT LEAST ONE MONO- OR DISACCHARIDE AND AT LEAST ONE CERAMIDE, AND METHODS

REFERENCE TO PRIOR APPLICATIONS

This application claims priority to U.S. provisional application 60/796,861 filed May 3, 2006, and to French patent application 0651187 filed Apr. 4, 2006, both incorporated herein by reference.

FIELD OF THE INVENTION

The present invention relates to a composition comprising at least one α-hydroxy acid, at least one mono- or disaccharide, and at least one ceramide compound. The composition is preferably a cosmetic composition. Preferred uses of the invention compositions include the treatment of keratinous substances, more particularly keratinous fibres and in particular the hair, and nontherapeutic treatment methods.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Hair formulations which make it possible to treat hair damaged by exposure to the weather or by physical (blow-drying, combing, and the like) or chemical (dyeing, bleaching, and the like) hair treatments are already known in the state of the art. Use has already been made, for this purpose, of ceramides or glycoceramides for the purpose of protecting the hair fibre. The application to hair of the latter compositions or of ceramides alone results, however, in inadequate cosmetic performances, on both wet hair and dry hair.

In the hair field, problems of breaking of hairs frequently arise when the latter are subjected to a simple mechanical treatment, such as brushing, combing or smoothing, it being possible for this type of treatment to be carried out in combination or not with concomitant or consecutive cosmetic treatments, such as hair straightening, shampooing, dyeing or perming. Furthermore, during mechanical treatments, such as blow-drying, the hairs are damaged by the heat of the dryer and the passage of the brush through the hairs in order to shape the hair.

The problems of breaking are furthermore particularly exacerbated in certain types of very curly hair where a phenomenon of premature breaking is observed (J. Soc. Cosmet. Chem., 36, January/February 1985, 39-52). Its high degree of curliness stands in the way of easy disentangling or smoothing and thus requires the application of greater mechanical stresses. For obvious reasons, these stresses significantly affect the mechanical strength of the hair and generally result in a high level of breakages.

Many hairs are thus broken during blow-drying. A search is thus underway for compositions which make it possible to protect the hair from breaking in this way during these assaults.

In order to prevent the phenomena of breakage of the individual hair, provision has already been made to treat hair with compounds of ceramide type.

Ceramides or their analogues are known to protect and/or repair the skin and/or hair fibres from assaults by the various agents and treatments mentioned above. In particular, they have a barrier effect which limits the escape of proteins; they also reinforce cuticular cohesion.

However, even if the ceramides prove to be effective, the protection or repair properties of the compositions comprising such compounds may still appear inadequate.

In particular, it is generally necessary to carry out several applications of the composition comprising ceramides.

Furthermore, it is also known that hydroxy acids have a reinforcing effect on the hair fibre. However, here again, it is generally necessary to carry out several applications of the composition in order to obtain satisfactory effects regarding breakage of the hair.

SUMMARY OF THE INVENTION

Unexpectedly, the inventors have found that the combination of ceramide, of α-hydroxy acid and of mono- and/or disaccharide prove to be particularly advantageous in preventing this phenomenon of breakage of hair while reducing the number of applications necessary. At the same time, a reduction is generally observed in the amount of hairs collected after an application followed by a blow-drying.

DETAILED DESCRIPTION OF THE PREFERRED EMBODIMENTS

More specifically, the inventors have found that, when using compositions comprising at least one hydroxy acid, at least one of a mono- and/or disaccharide and at least one ceramide compound, in particular on highly sensitive hair, an improvement in the mechanical strength of the hair is observed and the amount of hairs collected after blow-drying is markedly reduced.

In particular, a very good protective effect with regard to the breaking of the hair during blow-drying is obtained, an effect better than that obtained either with the hydroxy acid alone and the monosaccharide alone or with the ceramide compound alone, these compounds used at the total amounts of the compounds of the combination. Thus, the inventors have found in particular that the invention combination has a synergistic effect, which is not simply the addition of the properties of the three components. This discovery of synergy forms an unexpected aspect of the invention, and is expressed herein by the term "synergistic amounts" of at least one α-hydroxy acid, at least one of a mono- and/or disaccharide, and at least one ceramide compound.

One preferred subject-matter of the invention is thus a composition for topical application preferably intended for the treatment of keratinous substances, in particular keratinous fibres, especially the hair, wherein it comprises, in a cosmetically acceptable medium, at least one α-hydroxy acid, at least one monosaccharide and/or least one disaccharide, and at least one ceramide compound.

A further preferred subject-matter of the invention is the use of the compositions defined above in protecting keratinous substances, in particular keratinous fibres, especially the hair, from physical or chemical assaults and in particular with regard to blow-drying operations.

A further preferred subject-matter of the invention is the use of the compositions defined above in reducing the weight of hairs collecting during blow-drying operations.

The term "keratinous substance" according to the invention encompasses the skin, nails and keratinous fibres. The term "keratinous fibres" is understood the mean the hair, eyelashes, eyebrows and nonhead hairs.

The invention also relates to a method for caring for, reinforcing and/or repairing keratinous substances, wherein any one of the compositions defined above are applied to the keratinous substances, optionally followed by a rinsing operation.

The term "reinforcing and/or repairing keratinous substrates" according to the invention is understood to mean to retain and/or restore and/or improve the physical and/or mechanical properties of keratinous substrates, which can become apparent, for example:

either by better springiness and/or better resistance to tensile mechanical forces which are applied to them, for example during combing or blow-drying for keratinous fibres, in particular on African hair or any weakened or sensitized hair;

when the composition is applied to the nails, they are smoother and glossier;

when the composition is applied to the eyelashes, they are smoother, glossier, not so damaged and less brittle.

Ceramide Compounds

According to the present invention, the term "ceramide compound" is understood to mean natural or synthetic ceramides and/or glycoceramides and/or pseudoceramides and/or neoceramides.

Ceramide compounds are disclosed, for example, in patent Applications DE 4424530, DE 4424533, DE 4402929, DE 4420736, WO 95/23807, WO 94/07844, EP-A-0 646 572, WO 95/16665, FR-2 673 179, EP-A-0 227 994, WO 94/07844, WO 94/24097 and WO 94/10131, the teachings of which are included here by way of reference.

Ceramide compounds which can be used according to the present invention include, and in fact preferably correspond to, the general formula (I):

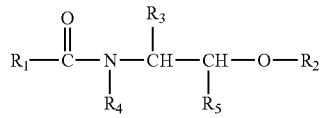

in which:

$R_1$ denotes:

either a saturated or unsaturated and linear or branched $C_1$-$C_{50}$, preferably $C_5$-$C_{50}$, hydrocarbon radical, it being possible for this radical to be substituted by one or more hydroxyl groups optionally esterified by an acid $R_7$COOH, $R_7$ being an optionally mono- or polyhydroxylated, saturated or unsaturated and linear or branched $C_1$-$C_{35}$ hydrocarbon radical, it being possible for the hydroxyl or hydroxyls of the $R_7$ radical to be esterified by an optionally mono- or polyhydroxylated, saturated or unsaturated and linear or branched $C_1$-$C_{35}$ fatty acid;

or an R"—(NR—CO)—R' radical, in which R denotes a hydrogen atom or a mono- or polyhydroxylated, preferably monohydroxylated, $C_1$-$C_{20}$ hydrocarbon radical, R' and R" are hydrocarbon radicals, the sum of the carbon atoms of which is between 9 and 30, R' being a divalent radical;

or an $R_8$—O—CO—$(CH_2)_p$ radical, in which $R_8$ denotes a $C_1$-$C_{20}$ hydrocarbon radical and p is an integer varying from 1 to 12;

$R_2$ is chosen from a hydrogen atom, a saccharide radical, in particular a $(glycosyl)_n$, $(galactosyl)_m$ or sulphogalactosyl radical, a sulphate or phosphate residue, a phosphorylethylamine radical and a phosphorylethylammonium radical, in which n is an integer varying from 1 to 4 and m is an integer varying from 1 to 8;

$R_3$ denotes a hydrogen atom or a hydroxylated or nonhydroxylated and saturated or unsaturated $C_1$-$C_{33}$ hydrocarbon radical, it being possible for the hydroxyl or hydroxyls to be esterified by an inorganic acid or an acid $R_7$COOH, $R_7$ having the same meanings as hereinabove, and it being possible for the hydroxyl or hydroxyls to be etherified by a $(glycosyl)_n$, $(galactosyl)_m$, (see above for n and m) sulphogalactosyl, phosphorylethylamine or phosphorylethylammonium radical, it also being possible for $R_3$ to be substituted by one or more $C_1$-$C_{14}$ alkyl radicals;

preferably, $R_3$ denotes a $C_{15}$-$C_{26}$ α-hydroxyalkyl radical, the hydroxyl group optionally being esterified by a $C_{16}$-$C_{30}$ α-hydroxy acid;

$R_4$ denotes a hydrogen atom, a methyl or ethyl radical, an optionally hydroxylated, saturated or unsaturated and linear or branched $C_3$-$C_{50}$ hydrocarbon radical or a —$CH_2$—CHOH—$CH_2$—O—$R_6$ radical, in which $R_6$ denotes a $C_{10}$-$C_{26}$ hydrocarbon radical, or an $R_8$—O—CO—$(CH_2)_p$ radical, in which $R_8$ denotes a $C_1$-$C_{20}$ hydrocarbon radical and p is an integer varying from 1 to 12;

$R_5$ denotes a hydrogen atom or an optionally mono- or polyhydroxylated, saturated or unsaturated and linear or branched $C_1$-$C_{30}$ hydrocarbon radical, it being possible for the hydroxyl or hydroxyls to be etherified by a $(glycosyl)_n$, $(galactosyl)_m$, (see above for n and m) sulphogalactosyl, phosphorylethylamine or phosphorylethylammonium radical;

with the proviso that, when $R_3$ and $R_5$ denote hydrogen or when $R_3$ denotes hydrogen and $R_5$ denotes methyl, then $R_4$ does not denote a hydrogen atom or a methyl or ethyl radical.

Preference is given, among the compounds of formula (I), to the ceramides and/or glycoceramides with the structure described by Downing in *Journal of Lipid Research*, Vol. 35, 2060-2068, 1994, or those disclosed in French Patent Application FR-2 673 179, the teachings of which are incorporated herein by reference.

The ceramide compounds which are more particularly preferred according to the invention are the compounds of formula (I) for which $R_1$ denotes an optionally hydroxylated and saturated or unsaturated alkyl derived from $C_{14}$-$C_{22}$ fatty acids; $R_2$ denotes a hydrogen atom; and $R_3$ denotes an optionally hydroxylated and linear $C_{11}$-$C_{17}$ radical and preferably $C_{13}$-$C_{15}$ radical. $R_3$ preferably denotes an α-hydroxycetyl radical and $R_2$, $R_4$ and $R_5$ denote a hydrogen atom.

Such compounds include, for example:
2-N-linoleoylaminooctadecane-1,3-diol,
2-N-oleoylaminooctadecane-1,3-diol (N-oleoyldihydro-sphingosine),
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
or the mixtures of these compounds.

Use may also be made of mixtures of ceramide compounds, such as, for example, the mixtures of ceramide(s) 2 and ceramide(s) 5 according to the Downing classification.

Particular use may also be made of the compounds of formula (I) for which $R_1$ denotes a saturated or unsaturated alkyl radical derived from $C_{12}$-$C_{22}$ fatty acids; $R_2$ denotes a galactosyl or sulphogalactosyl radical; and $R_3$ denotes a saturated or unsaturated $C_{12}$-$C_{22}$ hydrocarbon radical and preferably a —CH=CH—(CH$_2$)$_{12}$—CH$_3$ group.

Mention may be made, by way of example, of the product composed of a mixture of glycoceramides sold under the trade name Glycocer by Waitaki International Biosciences.

Use may also be made of the compounds of formula (I) disclosed in Patent Applications EP-A-0 227 994, EP-A-0 647 617, EP-A-0 736 522 and WO 94/07844.

Such compounds include, for example, Questamide H (bis (N-hydroxyethyl-N-cetyl)malonamide), sold by Quest, or the N-(2-hydroxyethyl)-N-(3-cetyloxy-2-hydroxy-propyl) amide of cetylic acid.

Use may also be made of N-docosanoyl-N-methyl-D-glucamine, disclosed in Patent Application WO 94/24097.

It is of course possible to use mixtures of the various ceramide compounds in the invention compositions.

The concentration of ceramide compounds is not specifically limited, and can for example vary from 0.0001% to 10% by weight approximately with respect to the total weight of the composition, preferably from 0.001 to 5% approximately and more preferably still from 0.005 to 1% by weight, better still from 0.0075 to 0.1% by weight.

Mono- and Disaccharide

The invention composition comprises at least one saccharide selected from the group of monosaccharides, disaccharides, and mixtures thereof. Advantageously, the monosaccharide is preferably chosen from glucose, fructose, galactose, mannose, talose, sorbose, xylose, lyxose, fucose, arabinose, rhamnose, ribose, ribulose, xylulose, or sorbitol. As regards the disaccharides, they are preferably chosen in particular from maltose, lactose, cellobiose, trehalose, sucrose.

These saccharides can exist in the form of L or D isomers. Preferably, the saccharide is a monosaccharide. More particularly, the monosaccharide is chosen from glucose, fructose and their mixtures, more particularly in the form of the D isomer. More particularly, the disaccharide is sucrose.

The concentration of the at least one saccharide selected from the group of monosaccharides, disaccharides, and mixtures thereof according to the invention is not specifically limited and can vary from, e.g., 0.05% to 10% by weight approximately with respect to the total weight of the composition, preferably from 0.1 to 5% approximately and more preferably still from 0.1 to 1% by weight.

α-Hydroxy Acid

The term "α-hydroxy acid" is understood to mean, according to the present invention, a carboxylic acid having at least one hydroxyl functional group occupying an α-position on said acid (carbon adjacent to a carboxylic acid functional group). This acid can be present in the final composition in the form of the free acid and/or in the form of one of its associated salts (salts with an organic base or an alkali metal, in particular), especially according to the final pH imposed on the composition.

The α-hydroxy acids (α-hydroxy acid) include, for example, citric acid, lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetracosanoic acid, 2-hydroxyeicosanoic acid, mandelic acid, phenyllactic acid, gluconic acid, galacturonic acid, aleuritic acid, ribonic acid, tartronic acid, tartaric acid, malic acid, fumaric acid, their salts and their mixtures. It is also possible to use mixtures of these various acids.

According to a preferred form, the α-hydroxy acid is chosen from citric acid, malic acid, tartaric acid, lactic acid and their salts. More particularly, the α-hydroxy acid is chosen from citric acid, lactic acid, their salts and their mixtures.

The α-hydroxy acid or acids are not limited with regard to amount, and can be present in an amount ranging, for example, from 0.001 to 10% by weight, from 0.005 to 5% by weight, preferably from 0.01 to 3% by weight and better still from 0.02 to 1% by weight, with respect to the total weight of the composition.

Preferably, the α-hydroxy acid(s)/mono- and/or disaccharide(s) ratio by weight ranges from 0.01 to 20, better still from 0.05 to 10 and more preferably from 0.1 to 1.

Preferably, the α-hydroxy acid(s)/ceramide compound(s) ratio by weight ranges from 1 to 200, better still from 1 to 20 and more preferably from 2 to 10.

Preferably, the mono- and/or disaccharide(s)/ceramide compound(s) ratio by weight ranges from 0.1 to 100, better still from 1 to 50 and more preferably from 20 to 50.

Optional Ingredients

The compositions of the invention advantageously additionally, but optionally, comprise at least one surface-active agent which is generally present in an amount of between 0.1% and 50% by weight approximately, preferably between 3% and 40% and more preferably still between 5% and 30%, with respect to the total weight of the composition.

This surface-active agent is preferably chosen from anionic, amphoteric, nonionic or cationic surface-active agents or their mixtures.

The surfactants which are particularly suitable for implementing the present invention include the following:

(i) Anionic Surfactant(s):

Mention may in particular be made, by way of example, of anionic surfactants which can be used, alone or as mixtures, in the context of the present invention, of (nonlimiting list) the salts (in particular alkali metal, especially sodium, salts, ammonium salts, amine salts, aminoalcohol salts or magnesium salts) of the following compounds: alkyl sulphates, alkyl ether sulphates, alkylamido ether sulphates, alkylarylpolyether sulphates, monoglyceride sulphates; alkylsulphonates, alkyl phosphates, alkylamidesulphonates, alkylarylsulphonates, α-olefin-sulphonates, paraffinsulphonates; alkyl sulpho-succinates, alkyl ether sulphosuccinates, alkylamide-sulphosuccinates; alkyl sulphosuccinamates; alkyl sulphoacetates; alkyl ether phosphates; acylsarcosinates; acylisethionates and N-acyltaurates, the alkyl or acyl radical of all these different compounds preferably comprising from 8 to 24 carbon atoms, and the aryl radical preferably denoting a phenyl or benzyl group. Mention may also be made, among the anionic surfactants which can also be used, of the salts of fatty acids, such as the salts of oleic, ricinoleic, palmitic and stearic acids, the acids of coconut oil or of hydrogenated coconut oil; and acyllactylates in which the acyl radical comprises 8 to 20 carbon atoms. Use may also be made of weakly anionic surfactants, such as alkyl-D-galactosideuronic acids and their salts, as well as polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$) alkylamido ether carboxylic acids and their salts, in particular those comprising from 2 to 50 ethylene oxide groups, and their mixtures.

Among anionic surfactants, it is preferable to use, according to the invention, alkyl sulphate and alkyl ether sulphate salts and their mixtures.

(ii) Nonionic Surfactant(s):

The nonionic surface-active agents are themselves also compounds which are well known per se (in this respect see in particular "Handbook of Surfactants" by M. R. Porter, published by Blackie & Son (Glasgow and London), 1991, pp. 116-178) and, in the context of the present invention, their nature does not assume any critical character. They can thus be chosen in particular from (nonlimiting list) fatty alcohols, α-diols, alkylphenols or acids which are polyethoxylated, polypropoxylated or polyglycerolated, having a fatty chain comprising, for example, 8 to 18 carbon atoms, it being possible for the number of ethylene oxide or propylene oxide groups to range in particular from 2 to 50 and it being possible for the number of glycerol groups to range in particular from 2 to 30. Mention may also be made of the copolymers of ethylene and propylene oxide and the condensates of ethylene and propylene oxide with fatty alcohols; polyethoxylated fatty amides preferably having from 2 to 30 mol of ethylene oxide, polyglycerolated fatty amides on average comprising 1 to 5 glycerol groups and in particular 1.5 to 4; polyethoxylated fatty amines preferably having 2 to 30 mol of ethylene oxide; oxyethylenated esters of sorbitan fatty acids having from 2 to 30 mol of ethylene oxide; sucrose esters of fatty acids, polyethylene glycol esters of fatty acids, alkylpolyglycosides, N-alkylglucamine derivatives, or amine oxides, such as oxides of $(C_{10}-C_{14})$alkylamines or N-acylaminopropylmorpholine oxides. It should be noted that alkylpolyglycosides constitute nonionic surfactants which come particularly well within the scope of the present invention.

(iii) Amphoteric Surfactant(s):

The amphoteric surface-active agents, the nature of which does not assume any critical character in the context of the present invention, may be in particular (nonlimiting list) derivatives of aliphatic secondary or tertiary amines in which the aliphatic radical is a linear or branched chain comprising 8 to 22 carbon atoms and comprising at least one water-solubilizing anionic group (for example carboxylate, sulphonate, sulphate, phosphate or phosphonate); mention may also be made of $(C_8-C_{20})$alkyl betaines, sulphobetaines, $(C_8-C_{20})$ alkyl amido$(C_1-C_6)$alkyl betaines or $(C_8-C_{20})$alkyl amido$(C_8-C_{20})$alkyl sulphobetaines.

Mention may be made, among the amine derivatives, of the products sold under the name Miranol, as disclosed in U.S. Pat. No. 2,528,378 and U.S. Pat. No. 2,781,354 and with structures:

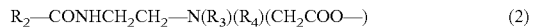

$$R_2\text{—CONHCH}_2\text{CH}_2\text{—N}(R_3)(R_4)(CH_2COO\text{—}) \quad (2)$$

in which: $R_2$ denotes an alkyl radical derived from an acid $R_2$—COOH present in hydrolysed coconut oil or a heptyl, nonyl or undecyl radical, $R_3$ denotes a β-hydroxyethyl group and $R_4$ a carboxymethyl group; and

$$R_5\text{—CONHCH}_2\text{CH}_2\text{—N}(B)(C) \quad (3)$$

in which:
B represents —CH$_2$CH$_2$OX', C represents —(CH$_2$)$_n$—Y', with
z=1 or 2,
X' denotes the —CH$_2$CH$_2$—COOH group or a hydrogen atom
Y' denotes —COOH or the —CH$_2$—CHOH—SO$_3$H radical
$R_5$ denotes an alkyl radical of an acid $R_9$—COOH present in hydrolysed linseed oil or coconut oil, an alkyl radical, in particular a $C_7$, $C_9$, $C_{11}$ or $C_{13}$ alkyl radical, a $C_{17}$ alkyl radical and its iso form or an unsaturated $C_{17}$ radical.

These compounds are classified in the CTFA dictionary, 5th Edition, 1993, under the names Disodium Cocoamphodiacetate, Disodium Lauroamphodiacetate, Disodium Caprylamphodiacetate, Disodium Caprylo-amphodiacetate, Disodium Cocoamphodipropionate, Disodium Lauroamphodipropionate, Disodium Caprylampho-dipropionate, Disodium Caryloamphodipropionate, Lauroamphodipropionic Acid and Cocoamphodipropionic Acid.

Mention may be made, by way of example, of the cocoamphodiacetate sold under the trade name Miranol C2M concentrate by Rhône-Poulenc.

Use may also be made of cationic surfactants, among which mention may in particular be made of (nonlimiting list): salts of primary, secondary or tertiary fatty amines, which amines are optionally polyoxyalkylenated; quaternary ammonium salts, such as tetraalkylammonium, alkylamidoalkyltrialkylammonium, trialkylbenzyl-ammonium, trialkylhydroxyalkylammonium or alkyl-pyridinium chlorides or bromides; imidazoline derivatives; or oxides of amines with a cationic nature.

The composition of the invention can also comprise at least one additive chosen from thickeners, fragrances, pearlescent agents, preservatives, sunscreens, anionic or nonionic or cationic or amphoteric polymers, proteins, protein hydrolysates, fatty acids with linear or branched $C_{16}$-$C_{40}$ chains, such as 18-methyleicosanoic acid, vitamins, panthenol, volatile or nonvolatile and organomodified or nonorganomodified silicones, vegetable, animal, mineral or synthetic oils and any other additive conventionally used in the cosmetics field which does not affect the properties of the compositions according to the invention.

The preferred silicones are aminated silicones and also polydimethylsiloxanes, in particular trimethylsilyl-polydimethylsiloxanes and polydimethylsiloxanes comprising dimethylsilanol end groups (dimethiconol).

The preferred cationic polymers are cationic guar gums and cationic celluloses.

These additives can be present in the composition according to the invention in proportions which are not limited, but which preferably fall in the range from 0 to 50% by weight, with respect to the total weight of the composition.

A preferred cosmetically acceptable medium can be composed solely of water or of a mixture of water and of at least one cosmetically acceptable solvent, such as a lower $C_1$-$C_4$ alcohol, such as ethanol, isopropanol, tert-butanol or n-butanol; alkylene glycols, such propylene glycol; polyol ethers; and their mixtures.

Preferably, the composition comprises from 50 to 95% by weight of water, with respect to the total weight of the composition.

The pH of the compositions is not limited but is generally between 2 and 12 and preferably between 4 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, preferably a carboxylic acid, such as, for example, citric acid.

The compositions in accordance with the invention can be used more particularly for washing or treating keratinous substances, such as the hair, skin, eyelashes, eyebrows, nails, lips or scalp and more particularly the hair.

In particular, the compositions according to the invention are detergent compositions, such as shampoos, shower gels or foam baths.

In this embodiment of the invention, the amount and the quality of the surfactants are those sufficient to confer, on the final composition, a satisfactory foaming and/or detergent power.

Thus, according to a preferred aspect of the invention, the surfactants can represent from 4% to 50% by weight, preferably from 6% to 35% by weight and more preferably still from 8% to 25% by weight of the total weight of the final composition.

The surfactant or surfactants can be chosen without distinction, alone or as mixtures, from the anionic, amphoteric and nonionic surfactants as defined above.

Use is preferably made, in the compositions in accordance with the invention, of mixtures of surface-active agents and in particular mixtures of anionic surface-active agents and mixtures of anionic surface-active agents and of amphoteric or nonionic surface-active agents. A particularly preferred mixture is a mixture composed of at least one anionic surface-active agent and of at least one amphoteric surface-active agent.

Use is preferably made of an anionic surface-active agent chosen from sodium, triethanolamine or ammonium ($C_{12}$-$C_{14}$) alkyl sulphates, sodium, magnesium, triethanolamine or ammonium ($C_{12}$-$C_{14}$)alkyl ether sulphates oxyethylenated with 2 to 5 mol of ethylene oxide, sodium cocoyl isethionate and sodium α-($C_{14}$-$C_{16}$)olefinsulphonate, and their mixtures with:
- either an amphoteric surface-active agent, such as the amine derivatives named disodium cocoamphodipropionate or sodium cocoamphopropionate sold in particular by Rhone-Poulenc under the commercial name "Miranol C2M Conc", as a 38% aqueous solution of active material, or under the name Miranol C32;
- or an amphoteric surface-active agent of zwitterionic type, such as alkyl betaines, in particular the coco betaine sold under the name "Dehyton AB 30" as a 32-aqueous solution of AM by Henkel, or alkyl amido betaines, in particular cocoamidopropyl betaines.

A further subject-matter of the invention is a method for the treatment of keratinous substances, such as the hair, wherein it comprises applying, to the keratinous substances, a composition as defined above and in then optionally rinsing with water.

Thus, the method according to the invention makes it possible to care for or wash the hair or any other keratinous substance.

The compositions of the invention can also be provided in the form of rinse-out or leave-in conditioners or of perming, hair-straightening, dyeing or bleaching compositions or alternatively in the form of rinse-out compositions to be applied before or after a dyeing, bleaching, perming or hair-straightening operation or alternatively between the two stages of a dyeing, perming or hair-straightening operation.

The compositions according to the invention can be used as leave-in products, in particular for the form retention of the hairstyle or the shaping or styling of the hair.

They are then more particularly hair-setting lotions, blow-drying lotions, fixing compositions (lacquers) and styling compositions.

The compositions of the invention can also be provided in the form of washing compositions for the skin and in particular in the form of bath or shower solutions or gels or of make-up-removing products.

The compositions according to the invention can also be provided in the form of aqueous or aqueous/alcoholic lotions for caring for the skin and/or hair.

The composition according to the invention can be used for making up keratinous substances. The make-up composition can be a nail varnish, a nail care composition, an eyeliner or a mascara and preferably a mascara. Thus, the composition is preferably a cosmetic composition.

The compositions according to the invention can be provided in any form, including in the form of a gel, milk, cream, lotion, stick, emulsion, thickened lotion or foam and can be used for the skin, nails, eyelashes, lips and more particularly hair and eyelashes.

The compositions can be packaged in any various forms, in particular in vaporizers, in pump-action sprays or in aerosol containers, in order to provide for application of the composition in the vaporized form or in the form of a foam. Such packaging forms are indicated, for example, when it is desired to obtain a spray, a lacquer or a foam for the treatment of the hair.

When the composition according to the invention is packaged in the aerosol form for the purpose of obtaining an aerosol foam or lacquer, it preferably comprises at least one propellant which can be chosen from volatile hydrocarbons, such as n-butane, propane, isobutane or pentane, a chlorinated and/or fluorinated hydrocarbon, and their mixtures. Use may also be made, as propellant, of carbon dioxide gas, nitrous oxide, dimethyl ether, nitrogen, compressed air and their mixtures.

In everything which follows or which precedes, the percentages expressed are by weight.

The invention will now be more fully illustrated using the following examples, which should not be regarded as limiting it to the embodiments described.

In the examples, AM means active material.

Example 1

The following shampooing composition was prepared:

|  | A | B |
|---|---|---|
| Lauryl ether sulphate comprising 2.2 mol of ethylene oxide as an aqueous solution comprising 70% of AM | 16 g AM | 16 g AM |
| Cocoylbetaine comprising 30% of AM | 1.8 g AM | 1.8 g AM |
| N-Oleoyldihydrosphingosine | 0.01 g | — |
| Citric acid | 0.05 g | 0.05 g |
| Lactic acid | 0.03 g | 0.03 g |
| Fructose | 0.25 g | 0.25 g |
| Glucose | 0.13 g | 0.13 g |
| Sucrose | 0.03 g | 0.03 g |
| Quaternized cellulose (JR 400 from Amerchol) | 0.36 g | 0.36 g |
| Ethylene glycol distearate | 2 g | 2 g |
| Polydimethylsiloxane (Mirasil DM 500 000 from Rhodia) | 1 g | 1 g |
| Coconut acid monoisopropanolamide | 1.13 g | 1.13 g |
| Sodium glycolate | 0.12 g | 0.12 g |
| Sodium N-cocoylamidoethyl-N-(ethoxycarboxymethyl)glycinate | 0.62 g AM | 0.62 g AM |
| Preservatives | q.s. | q.s. |
| Fragrance | q.s. | q.s. |
| Water q.s. for | 100 g | 100 g |

Blow-Drying Test 1 g of composition is applied to prewashed and predried locks of hair weighing 2.7 g. The composition is caused to foam. After a leave-in time of 5 minutes, the locks are rinsed with water.

Blow-drying is carried out on the superficially dried hair using a brush and a hairdryer. Blow-drying is carried out while passing the brush from the root to the end. The broken hairs are meticulously recovered on the brush using a comb and then they are weighed. The weight of hairs recovered for a lock is reduced to the weight of hairs recovered for one gram of starting hair.

The weight of hairs recovered for compositions A and B was compared. The greater the weight of broken hairs, the less the composition protects the hair.

The results are collated in the table below:

|  | Compositions tested | |
| --- | --- | --- |
|  | A<br>Invention | B<br>Comparative |
| Weight of hairs recovered on the brush after blow-drying | 12.8 mg/g | 21.6 mg/g |

It is noticed that the weight of hairs recovered on the brush after blow-drying is markedly reduced (−40%) for the composition according to the invention A simultaneously comprising ceramide, saccharide and α-hydroxy acid.

Examples 2 and 3

The following shampooing compositions can be prepared:

|  | 2 | 3 |
| --- | --- | --- |
| Lauryl ether sulphate comprising 2.2 mol of ethylene oxide as an aqueous solution comprising 70% of AM | 14 g AM | 15.4 g AM |
| Sodium N-cocoylamidoethyl-N-(ethoxy-carboxymethyl)glycinate | 2.4 g AM | — |
| Cocoamidopropyl betaine comprising 30% of AM | — | 2.4 g AM |
| Sodium chloride | — | 0.75 g |
| N-Oleoyldihydrosphingosine | 0.1 g | — |
| N-Stearoylphytosphingosine | — | 0.05 g |
| Tartaric acid | 0.5 g | — |
| Malic acid | — | 0.2 g |
| Galactose | — | 1 g |
| Xylose | 0.1 g | — |
| Distearyl ether | — | 1.5 g |
| Mixture of $C_{18}$-$C_{22}$ fatty alcohols (Nafol 1822C) | — | 1.5 g |
| Lauryl alcohol comprising 2.5 mol of ethylene oxide | — | 0.9 g |
| (Hydroxypropylguar)trimethylammonium chloride | 0.2 g | 0.1 g |
| Ethylene glycol distearate | 2.5 g | — |
| Polydimethylsiloxane (Dow Corning 200 Fluid from Dow Corning) | 2.5 g | 2.5 g |
| Coconut acid monoisopropanolamide | 1.4 g | 1.5 g |
| Crosslinked polyacrylic acid (Carbopol 980 from Noveon) | 0.15 g | 0.2 g |
| Hexylene glycol | 0.6 g | — |
| Preservatives | q.s. | q.s. |
| Fragrance | q.s. | q.s. |
| Water q.s. for | 100 g | 100 g |

Example 4

The following mascara composition can be prepared:

| Beeswax | 25% |
| --- | --- |
| Stearic acid | 5.82% |
| Triethanolamine | 2.4% |
| Hydroxyethylcellulose | 0.9% |
| Gum arabic | 3.4% |
| Black iron oxide | 7% |
| N-Oleoyldihydrosphingosine | 0.1% |
| Fructose | 0.3% |
| Citric acid | 0.5% |
| Preservatives | q.s. |
| Water q.s. for | 100% |

The above written description of the invention provides a manner and process of making and using it such that any person skilled in this art is enabled to make and use the same, this enablement being provided in particular for the subject matter of the appended claims, which make up a part of the original description and including a composition for topical application intended for the treatment of keratinous substances, in particular keratinous fibres, especially the hair, wherein it comprises, in a cosmetically acceptable medium, at least one saccharide selected from the group consisting of monosaccharides, disaccharides, and mixtures thereof, at least one α-hydroxy acid, and at least one ceramide compound.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The invention method and composition is preferably used by subjects desirous of the benefits noted herein, subjects "in need of" these benefits. Such subjects are typically desirous of reinforcing and/or repairing keratinous substrates, meaning retaining and/or restoring and/or improving the physical and/or mechanical properties of keratinous substrates, which can become apparent, for example:

either by better springiness and/or better resistance to tensile mechanical forces which are applied to them, for example during combing or blow-drying for keratinous fibres, in particular on African hair or any weakened or sensitized hair;

when the composition is applied to the nails, they are smoother and glossier;

when the composition is applied to the eyelashes, they are smoother, glossier, not so damaged and less brittle.

Typically, one using the invention compositions as disclosed will use them in amounts to obtain one of the noted benefits. Such amount is inclusive of an amount of the compositions described herein at the disclosed concentrations of active ingredients sufficient to cover the area being treated in a single application, and of course includes that amount applied upon repeated application, for example on a daily basis over a course of days, weeks, etc. In a preferred embodiment the invention process includes multiple applications of the invention composition to the area(s) in need of attention.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition comprising:
at least one α-hydroxy acid selected from the group consisting of citric acid, lactic acid, salts thereof, and mixtures thereof;
at least one saccharide selected from the group consisting of glucose, fructose, sucrose, and mixtures thereof;
at least one ceramide compound comprising 2-N-oleoylaminooctadecane-1,3-diol; and 50-95 wt. % of water, based on a total weight of the composition,
wherein a weight ratio of the at least one saccharide to the at least one ceramide compound is from 1 to 50.

2. The composition according to claim 1, wherein the at least one ceramide compound further comprises one or more ceramide compounds selected from the group consisting of: 2-N-linoleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4-triol; 2-N-palmitoylaminohexadecane-1,3-diol; and mixtures thereof.

3. The composition according to claim 1, wherein the at least one ceramide compound is present in an amount of 0.0001-10 wt. %, based on the total weight of the composition.

4. The composition according to claim 1, wherein the at least one saccharide is sucrose or a mixture of glucose, fructose and sucrose.

5. The composition according to claim 1, wherein the at least one saccharide is selected from the group consisting of D-glucose, D-fructose, sucrose and mixtures thereof.

6. The composition according to claim 1, wherein the at least one saccharide is present in an amount of 0.05-10 wt. %, based on the total weight of the composition.

7. The composition according to claim 1, wherein the at least one α-hydroxy acid is citric acid or a salt thereof.

8. The composition according to claim 1, wherein the at least one α-hydroxy acid is a mixture of citric acid and lactic acid, or salts thereof.

9. The composition according to claim 1, wherein the at least one α-hydroxy acid is present in an amount of 0.001-10 wt. %, based on the total weight of the composition.

10. The composition according to claim 1, wherein a weight ratio of the at least one α-hydroxy acid to the at least one saccharide is from 0.01 to 20.

11. The composition according to claim 1, wherein a weight ratio of the at least one α-hydroxy acid to the at least one ceramide compound is from 1 to 200.

12. The composition according to claim 1, further comprising at least one surface-active agent selected from the group consisting of an anionic surfactant, a cationic surfactant, a nonionic surfactant, an amphoteric surfactant, and mixtures thereof.

13. The composition according to claim 12, wherein the at least one surface-active agent is present in an amount of 0.1-60 wt. %, based on the total weight of the composition.

14. The composition according to claim 1, further comprising at least one additive selected from the group consisting of thickeners, fragrances, pearlescent agents, preservatives, sunscreens, anionic or nonionic or cationic or amphoteric polymers, proteins, protein hydrolysates, fatty acids with linear or branched $C_{16}$-$C_{40}$ chains, volatile or nonvolatile and organomodified or nonorganomodified silicones, vitamins, panthenol, fatty esters and mixtures thereof.

15. The composition according to claim 1, further comprising at least one cationic polymer.

16. The composition according to claim 1, further comprising at least one silicone.

17. The composition according to claim 1, further comprising at least one cosmetically acceptable solvent.

18. The composition according to claim 17, wherein the at least one cosmetically acceptable solvent is selected from the group consisting of monoalcohols, polyalcohols, polyol ethers, and mixtures thereof.

19. The composition according to claim 1, which is in the form of a shampoo, conditioner, composition for perming, straightening, dyeing or bleaching the hair, rinse-out composition to be applied between the two stages of a dyeing, perming or hair-straightening operation, or washing composition for the skin.

20. The composition according to claim 1, comprising synergistic amounts of the at least one α-hydroxy acid, the at least one saccharide, and the at least one ceramide compound, to thereby impart a synergistic hair strengthening property to the composition.

21. The composition according to claim 1, wherein the weight ratio of the at least one saccharide to the at least one ceramide compound is from 1 to 20.

22. The composition according to claim 1, wherein the weight ratio of the at least one saccharide to the at least one ceramide compound is from 20 to 50.

23. The composition according to claim 1, consisting essentially of:
at least one α-hydroxy acid selected from the group consisting of citric acid, lactic acid, salts thereof, and mixtures thereof;
at least one saccharide selected from the group consisting of glucose, fructose, sucrose, and mixtures thereof;
2-N-oleoylaminooctadecane-1,3-diol; and
50-95 wt. % of water, based on a total weight of the composition,
wherein a weight ratio of the at least one saccharide to the at least one ceramide compound is from 1 to 50.

24. A method of strengthening hair comprising applying to a keratinous substance the composition according to claim 1, optionally followed by rinsing with water.

* * * * *